(12) United States Patent
Britto

(10) Patent No.: US 7,569,031 B2
(45) Date of Patent: Aug. 4, 2009

(54) BREAST PUMP

(75) Inventor: James Joseph Britto, Westport, MA (US)

(73) Assignee: The First Years Inc., Avon, MA (US)

( * ) Notice: Subject to any disclaimer, the term of this patent is extended or adjusted under 35 U.S.C. 154(b) by 0 days.

(21) Appl. No.: 10/873,520

(22) Filed: Jun. 22, 2004

(65) Prior Publication Data

US 2005/0283112 A1 Dec. 22, 2005

(51) Int. Cl.
*A61M 1/06* (2006.01)
*A61M 1/00* (2006.01)

(52) U.S. Cl. .......................... 604/74; 604/315

(58) Field of Classification Search ............. 604/73–76, 604/313–316
See application file for complete search history.

(56) References Cited

U.S. PATENT DOCUMENTS

| | | | |
|---|---|---|---|
| 3,238,937 A * | 3/1966 | Stein ............................ 601/14 |
| 5,100,406 A | 3/1992 | Panchula |
| 5,885,246 A | 3/1999 | Ford |
| 5,947,923 A * | 9/1999 | Uehara et al. .................. 604/74 |
| 6,045,529 A | 4/2000 | Nüesch |
| 6,139,521 A | 10/2000 | Larsson |
| 6,257,847 B1 | 7/2001 | Silver et al. |
| 6,355,012 B1 * | 3/2002 | Nuesch .......................... 604/74 |
| 6,387,072 B1 | 5/2002 | Larsson et al. |
| 6,461,324 B1 | 10/2002 | Schlensog |
| 6,579,258 B1 | 6/2003 | Atkin et al. |
| 6,663,587 B2 | 12/2003 | Silver et al. |
| 6,673,036 B1 | 1/2004 | Britto |
| 6,676,631 B1 | 1/2004 | Greter |
| 6,706,012 B2 * | 3/2004 | McKendry et al. ............ 604/74 |
| 6,964,651 B1 * | 11/2005 | McKendry ..................... 604/74 |
| 7,160,273 B2 | 1/2007 | Greter et al. |
| 2001/0038799 A1 | 11/2001 | Silver et al. |
| 2002/0062103 A1 | 5/2002 | Larsson et al. |
| 2002/0072701 A1 | 6/2002 | Nuesch |
| 2003/0069536 A1 | 4/2003 | Greter et al. |
| 2005/0159701 A1 | 7/2005 | Conaway |

* cited by examiner

*Primary Examiner*—Kevin C Sirmons
*Assistant Examiner*—Andrew M Gilbert
(74) *Attorney, Agent, or Firm*—Michael Best & Friedrich LLP

(57) ABSTRACT

A portable pumping device for drawing milk from a human breast includes a breast shield adapted to fit over a nipple of a breast and a flow line coupled to the breast shield. The flow line is adapted to allow air to flow there through a pump coupled to the breast shield via the flow line. The pump includes a pump intake and a pump exhaust and is operable to create a pressure drop between the nipple and the pump, wherein the pressure drop creates a suction at the breast shield by lowering the pressure of air in the flow line. A blow-back valve is disposed between the flow line and the pump. The blow-back valve has a valve piston disposed in a valve housing The valve housing includes a flow line aperture that communicates via the flow line with the breast shield, a valve inlet adapted to communicate external to the flow line, and a valve exhaust adapted to communicate external to the flow line. The valve piston is adapted to alternatively seal the valve inlet and the valve exhaust.

17 Claims, 8 Drawing Sheets

BREAST PUMP

TECHNICAL FIELD

This invention relates to breast pumps, and more particularly to electric breast pumps with valves for cycling action.

BACKGROUND

Many parents desire to feed their infants, or have their infants fed, with breast milk from the birth mother. Occasionally, a breast-milk provider is unavailable to provide direct breast-feeding to the infant, and must therefore use prepumped breast milk stored in a bottle to feed the infant. Though numerous types of breast pumps exist, the easier the pump is for the provider to operate, the more relaxed, and therefore productive, the mother can be. Additionally, the more the pumping action of the pump replicates or resembles the sucking rhythm of an infant, the more easily milk will flow into a collection container.

Automated breast pumps generally operate with an electric motor that operates a pump such as a diaphragm or piston. Most hand-held automated pumps include a valve that opens the suction area between the breast and the pump to the external atmosphere. A motor drives a pumping mechanism so that the pump constantly attempts to remove air from between the pump intake and the breast. To simulate the suckling of an infant, the valve is alternatively opened and closed during pump operation. When the valve is closed, a pressure drop is created between the pump intake and the breast, and thus suction from the pump to the breast through a tube or hose. When the valve is opened, the suction is released to allow the breast to recover prior to the following suction cycle. During the suction cycle, the breast milk is drawn from the breast and falls through a flapper valve and into a collection article, such as a bottle.

To simulate the sucking rhythm of an infant, the valve is cycled open and closed for periods of time, usually only a few seconds each, to alternatively provide suction and release suction to the breast. Opening the valve allows the suction to the breast to be eliminated, but it takes time for the outside air to bleed into the system to fill the void created by the suction of the pump. The amount of time required to equalize pressure between the breast and the pump and the external atmosphere may depend on a number of criteria, such as the length of the tubing, the power of the pump motor, as well as other factors.

Additionally, some of the breast milk may pass beyond the flapper valve and fill the tubing between the collection bottle and the pump. Opening the valve may assist in allowing this breast milk to enter the bottle, but the likelihood of the breast milk in the tubing between the collection bottle and the pump being directed into the bottle upon the opening of the valve, and the normalization of pressure may depend on the length of the tubing, the positioning of the valve, and numerous other factors.

SUMMARY

According to one aspect of the invention, a portable pumping device for drawing milk from a human breast includes a breast shield adapted to fit over the nipple of a breast, a flow line coupled to the breast shield and a pump, so the pump is operable to create a pressure drop or suction between the nipple and the pump in the flow line. A blowback valve is disposed in the flow line between the breast shield and the pump. The blowback valve includes a first aperture that communicates via the flow line with the breast shield, and a second aperture that is adapted to communicate external to the flow line, and an exhaust, which is adapted to communicate external to the flow line. The valve piston is adapted to alternatively seal the second aperture and the exhaust. The system may be arranged such that sealing the second aperture creates suction at the breast shield and allows gases evacuated from the flow line to be dispelled to the exhaust. Additionally, or alternatively, the system may be arranged such that sealing the exhaust draws air through the second aperture and creates a pressure increase between the first aperture and the breast shield.

According to another implementation, a system for drawing milk from a human breast includes at least one pump module. Each of the at least one pump modules has a pump intake and a pump exhaust, and the pump intake and the pump exhaust are adapted to direct the flow of air through the at least one pump module. An intake line is coupled to the pump intake, an exhaust line coupled to the pump exhaust, and a valve piston is disposed in a valve housing. The valve piston has an intake seal and an exhaust seal, and the intake seal and the exhaust seal are coupled to a valve plunger. The intake seal is operable to seal an a valve inlet in the valve housing, and the exhaust seal is operable to seal a valve exhaust in the valve housing. A flow line aperture is disposed in the valve housing between the intake seal and the exhaust seal. The flow line aperture communicates an air flow between the pump module(s) and a breast shield coupled to the valve housing via a flow line. Additional and/or alternative implementations of the invention may include a cam coupled to the valve piston, so that the rotation of the cam causes the valve piston to move back and forth within the valve housing. According to this implementation, forming a seal between the valve inlet and the intake line and forming a seal between the exhuast line and the sub-housing connector creates a suction between the pump module and the breast shield. Additionally, a valve spring may be included that is loaded through the rotation of the cam. Upon the continued rotation of the cam, the valve piston moves back and forth within the vavle housing.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
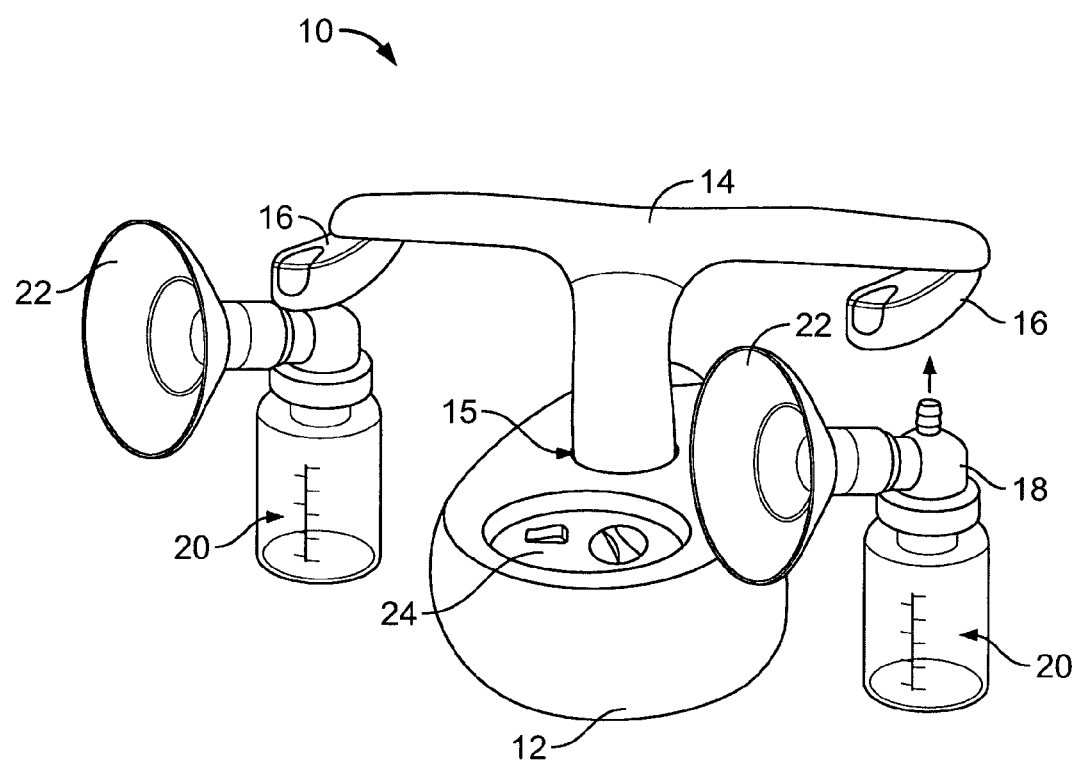
FIG. 1 is a respective view of a breast pump.

Referring to FIG. 1, a portable pumping device 10 includes a base 12, and a pump handle 14 insertable into a recess 15 formed in the base 12. Bottle couplers 16 are positioned at the distal ends of the pump handle 14 and are adapted to a vacuum bulkhead 18. The vacuum bulkhead 18 may be any suitable vacuum bulkhead, such as the vacuum bulkhead described in U.S. Pat. No. 6,673,036 B1 issued to Britto. Other types of vacuum bulkheads, collection devices, and bottle couplers may also be used in various implementations. The vacuum bulkhead 18 is adapted to connect to a collection bottle 20, and a breast shield 22. A control panel 24 may also be included. The control panel 24 may provide a power switch, a side-selector that allows an operator to select a single side for pumping or both sides for pumping, or other suitable controls. Additionally, the pumping device may operate on A/C or D/C (not explicitly shown). Accordingly, the control panel 24 may provide for selectivity if the operator desires to operate in one power mode or the other.

Figure 2:
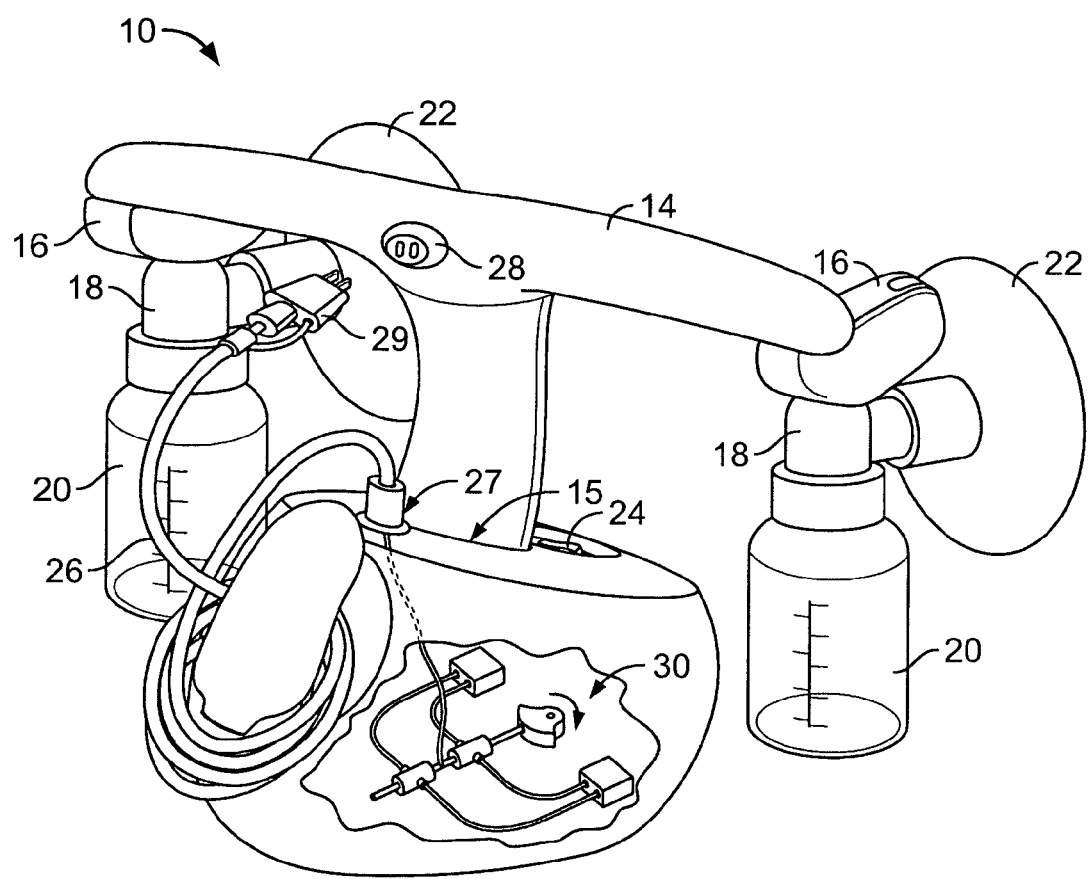
FIG. 2 is a reverse view of the breast pump of FIG. 1, including a cut-away portion that allows a view of the pump and valve system.

FIG. 2 illustrates a reverse or rear view of the portable pumping device 10 as illustrated in FIG. 1. Additionally, FIG. 2 shows a cut-away portion of the base 12, which displays a valve/pump assembly 30 disposed in the base 12. In addition to the features discussed above with respect to FIG. 1, FIG. 2 illustrates a conduit or flow line 26 that extends from the pump/valve assembly 30 to a flow line adaptor 28 via a flow line plug 29 to the handle 14. The flow line 26 extends into the handle 14 to hydraulically couple the pump/valve assembly 30 to the breast shields 22. During operation, the flow line 26 is adapted to communicate the alternating suction and over pressure, described below, provided by the pump/valve assembly 30 during the operation of the pump to generate suction to express breast milk.

Figure 3:
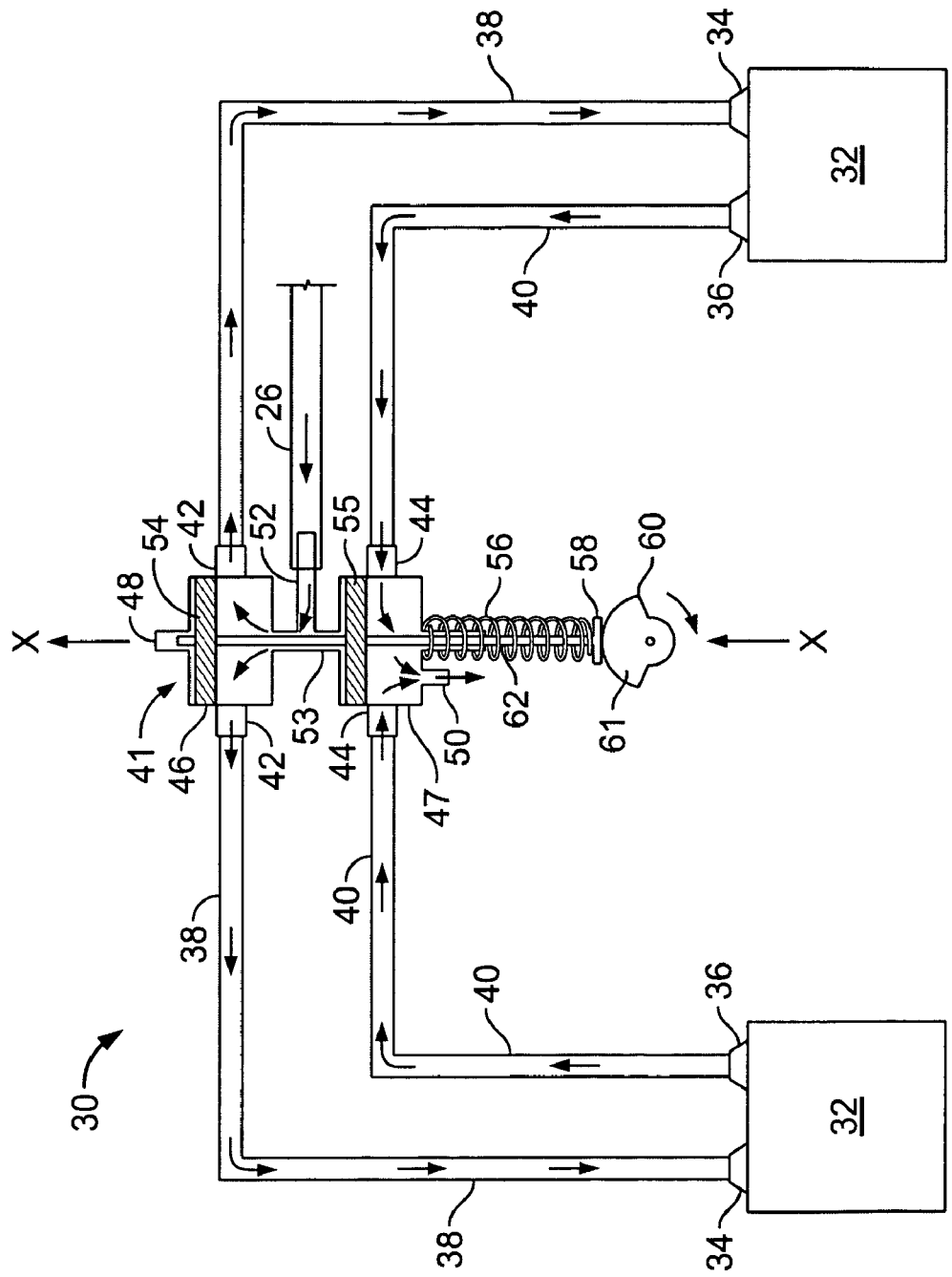
FIG. 3 is a plan view of a pump and valve system that includes two pump modules.

FIG. 3 illustrates the pump/valve assembly 30 that is disposed within the base 12 of FIG. 2. In the implementation shown, the pump/valve assembly includes two pump modules 32, each pump module 32 including an intake 34 and an exhaust 36. Alternatively, any number of pump modules 32 could be added to the pump/valve assembly 30. For example, there could be a single pump module 32 or more than two pump modules 32 in various implementations of the invention.

An intake line 38 is coupled to the intake 34, and likewise an exhaust line 40 is coupled to the exhaust 36. The intake line 38 and the exhaust line 40 are coupled to a blow-back valve 41. The blow-back valve housing 41 includes intake line couplings 42, exhaust line couplings 44, a valve inlet 48, and a valve exhaust 50. An intake sub-housing 46 is disposed in or coupled to the intake line 38, and an exhaust sub-housing 47 is disposed in or coupled to the exhaust line 40. A sub-housing connector 53 is disposed between the intake sub-housing 46 and the exhaust sub-housing 47 and communicates between the interior of each. Accordingly, the intake line coupling 42 is disposed so that air can communicate with the interior of the intake sub-housing via the intake line 38 and thus the intake 34 of the pump 32. Likewise, the exhaust sub-housing includes the exhaust line couplings 44 disposed so that air may communicate with the interior of the exhaust sub-housing 41 with the exhaust line 40 and therefore, the exhaust 36 of the pump module 32.

A flow line aperture 52 is disposed through a wall of the sub-housing connector 53 between the intake sub-housing 46 and the exhaust sub-housing 47 of the blow-back valve 41. The flow line aperture 52 is adapted to be coupled to the flow line 26 that communicates from the blow-back valve 41 to the breast shield 22 as depicted in FIGS. 1 and 2. During operation of the pump/valve assembly 30, the alternate sealing of the intake 48 and the exhaust 50 provides alternating suction from, and over-pressure to, the breast shield 22 (described in greater detail below).

Disposed within each of the intake sub-housing 46 and the exhaust sub-housing 47 are an intake seal 54 and an exhaust seal 55, respectively, coupled to a valve plunger 62. The valve seals 54 and 55 may be manufactured from any suitable seal material. For example the valve seals 54 and 55 could be manufactured from rubber, either natural or synthetic, plastic, nylon, or other polymer, cellulose-based material, such as leather or paper, felt, or other suitable valve seal material.

In the implementation shown, the valve seals 54 and 55 and the valve plunger are substantially aligned along a valve axis "X". The valve plunger 62 is coupled to a valve cam 60 that is adapted to rotate in either a clockwise or counter clockwise direction. The valve cam 60 may have a valve lobe 61 which is a portion of the valve cam 60 having a radius larger than other portions of the valve cam 60. The valve plunger 62 connects the two valve seals 54 and 55 between the intake sub-housing and the exhaust sub-housing 47 through the sub-housing connector 53. Accordingly, the valve plunger 62 must be of sufficiently small dimensions to pass through the sub-housing connector 53 in addition to some space between the valve plunger 62 and the interior wall of the sub-housing connector 53.

The rotation of the valve cam 60 in either a clockwise or counter-clockwise direction causes movement of the valve plunger 62 along the valve axis, such that the valve seals 54 and 55 move back and forth within the intake sub-housing 46 and exhaust sub-housing 47, respectively. The movement of the valve plunger 62 is caused by the lobe 61 in contact with a cam follower 58. When the cam follower 58 engages the lobe 61 as the cam 60 rotates, the valve plunger 62 moves along the X axis toward the valve housing 41. In the implementation shown, the lobe 61 is in contact with the cam follower 58 for substantially the same amount of time as the non-lobe portion during the rotation of the cam 60, if the cam maintains a constant angular velocity. In the implementation shown, the phases of suction and overpressure are 180° opposite, and the suction/over-pressure ratio is approximately 1:1. If the percentage of the circumference dedicated to the lobe 61 is changed, the ratio of suction/over-pressure also changes, if the angular velocity of the cam 60 remains constant. Thus, if the lobe 61 is in contact with the cam follower for more time than the non-lobe portion, then in the configuration illustrated, the suction cycle is longer than the over-pressure cycle. If the phase is changed by 180°, then the suction cycle is shorter than the over-pressure cycle.

A valve spring 56 may be disposed between the exhaust sub-housing 47 and the cam follower 58 disposed between the cam and the exhaust sub-housing 47. The valve spring 56 illustrated in FIG. 3 is a coil-type spring. In various implementations, a number of suitable springs may be used. For example, the valve-spring 56 could be manufactured from a polymer, nylon, or other plastic. Additionally, instead of, or in addition to, a coil spring, the valve-spring could comprise a spring system that includes a spring arm manufactured from a metal, metal allow, polymer, nylon, or other plastic. Also, the valve-spring 56, though illustrated as disposed between the exhaust sub-housing and the cam follower 58, could be positioned at any appropriate position that allows the rotation of the cam—and therefore the movement of the valve plunger 62 toward the valve inlet 48—to place a load on the valve spring 56.

In the implementation shown, the cam follower 58 may be either formed as part of the valve plunger 62 or coupled to the valve plunger 62. In operation, the valve-spring 56 provides a load on the valve plunger and the cam such that as the cam rotates the valve seals 54 move back and forth within the intake sub-housing 46 and the exhaust sub-housing 47. The valve plunger 62 and the valve seals 54 and 55 may collectively be referred to as the valve piston 64. For purposes of describing the implementation illustrated by FIG. 3, as well as FIGS. 4A and 4B below, the valve piston 64 may be said to reach a "zenith" when the intake seal 54 disposed within the intake sub-housing 46 is disposed against the valve inlet 48, thus sealing valve inlet 48 from the interior of the blow-back valve 41. Alternatively, the valve piston reaches its "nadir" when the exhaust seal 54 disposed within the exhaust sub-housing is disposed against the valve exhaust 50, thus sealing the valve exhaust 50 from the interior of the blow-back valve 41.

The rotation of the cam 60 forces the valve plunger 62 toward the valve inlet 48, through the contact of the cam follower 58 with the cam 60. The valve seals 54 and 55 may be of sufficient dimensions to seal the intake line 38 from the valve inlet 48 and the exhaust line 40 from the exhaust 50, respectively prior to reaching the zenith and the nadir. For example, in the configuration illustrated in FIG. 3, upon passing the intake line coupling 42, the intake seal 54 may form a seal with the interior wall between the valve inlet 48 and the intake line 38 so that no air or fluid can pass from the valve inlet 48 and the intake line 38. Simultaneously, after the exhaust seal 55 within the exhaust sub-housing 47 moves past the exhaust line coupling 44 toward the sub-housing connector 53, the exhaust line 40 may be prevented from communicating with the flow line aperture 52. In this configuration, the flow line aperture 52 communicates with the intake 34 of the pump modules 32 so that a pressure drop, and therefore a suction, is formed between the pump modules 32 and the breast shield 22 via the flow line 26 (see FIG. 2).

Upon reaching the zenith, the valve may remain in place for a period of time dependent upon the shape of the cam 60 or the compression characteristics of the valve seal 54. For example, a cam 60 with non-uniform diameter (not shown) may permit the valve piston to remain at the zenith for a longer period of time than a valve cam 60 with a substantially circular cross-section. Upon further rotation of the cam 60, the valve piston begins to retreat from the valve-inlet 48 when the cam follower 58 is no longer in contact with the lobe 61 of the cam 60. Upon the movement of the valve piston toward the cam, the valve seal 54 disposed within the exhaust sub-housing 47 is biased toward the exhaust 50 in the valve sub-housing 47. Upon removing the valve seal 54 from the valve inlet 48, the seal between the valve inlet 48 and the inlet sub-housing 46 may be removed. Alternatively, the seal between the valve inlet 48 and the intake line 38 may remain until the intake seal passes to the opposite side of the intake line 38 from the valve inlet 48.

Figure 4A:
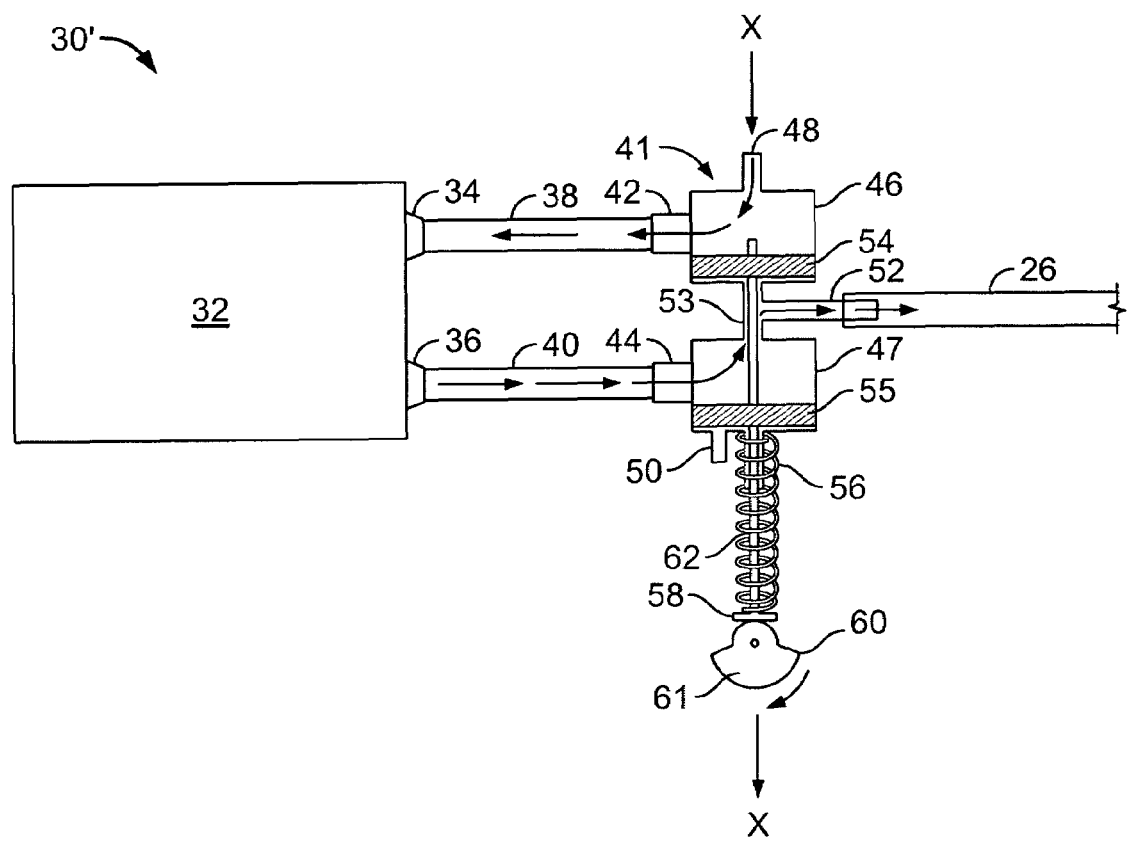
FIG. 4A is a pump and valve system that includes a single pump module and illustrates the pump-state of a positive pressure position.
Figure 4B:
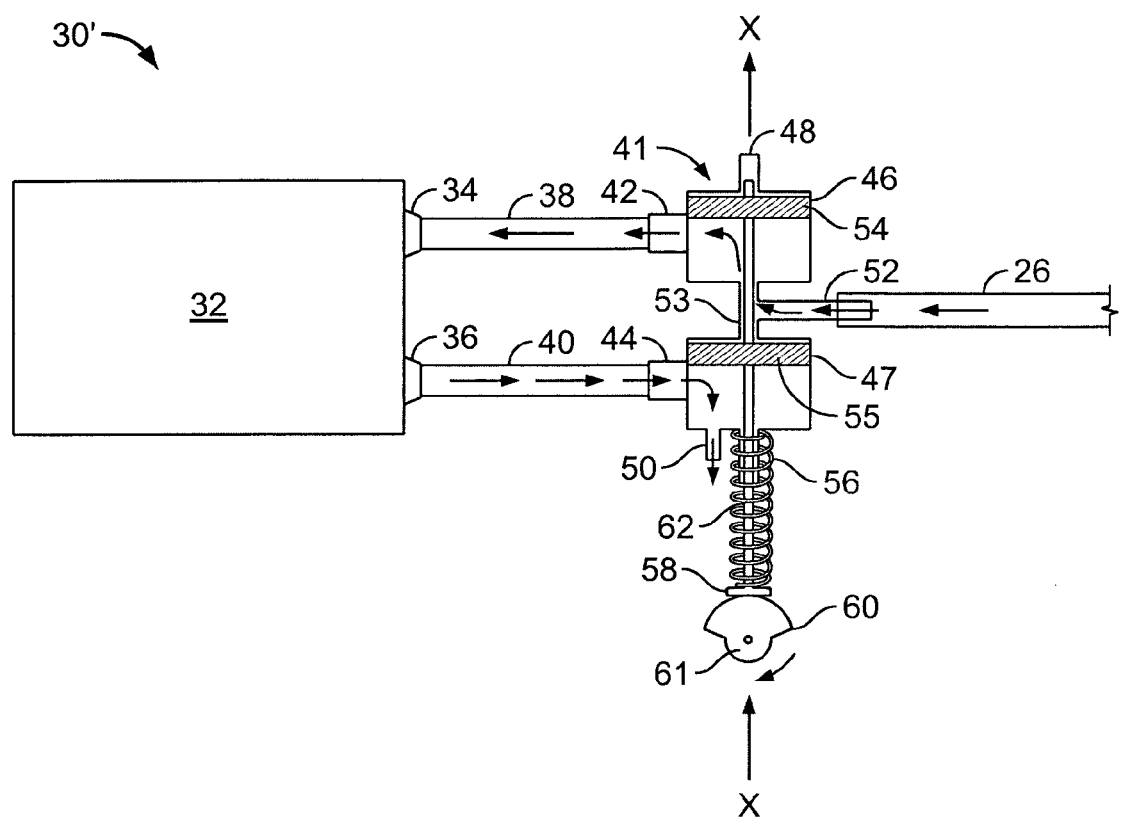
FIG. 4B is a plan view of a single module pump and valve system in which the valve is configured in a suction mode.

FIGS. 4a and 4b illustrate a valve/pump assembly 30' in which a single pump module 32 is provided. Additionally, FIGS. 4a and 4b illustrate the range of operation of the pump/valve assembly 30', and could be extrapolated to provide an understanding for the operation of the pump/valve assembly 30 illustrated by FIG. 3, as well as alternative pump/valve assembly configurations that include a plurality of pump modules 32 could be implemented in a pump/valve assembly according to implementations of the present invention. Accordingly, the like numbered components of the pump/valve assembly 30' indicates similar components as illustrated above with respect to FIG. 3.

FIG. 4A illustrates the pump/valve assembly 30' in the configuration in which the intake seal 54 disposed within the intake sub-housing 46 and the exhaust sub-housing 47 is at its nadir, and thus the exhaust seal 54 disposed within the exhaust sub-housing 47 is in position to seal exhaust 50 from the remainder of the blow-back valve 41 and provide communication between the exhaust 36 of the pump module 32 and the flow line aperture 52. This communication illustrated by FIG. 4A results in an over pressure between the pump module 32 and the breast shield 22 (see FIGS. 1 and 2). Accordingly, if the pump module 32 is engaged, air shown by arrows within the blow-back valve 41, the intake line 38, and the exhaust line 40, flows through various configurations of the valve/pump assembly 30'. Therefore, in the configuration illustrated by FIG. 4A, the exhaust is sealed by the exhaust seal 55 disposed within the exhaust sub-housing 47, and the air flowing from the exhaust 36 is forced through the exhaust sub-housing 47 through the sub-housing connector 53 and out the flow line aperture 52 to the flow line 26.

The position of the exhaust seal 55 in the exhaust sub-housing 47 between the exhaust line 40 and the valve exhaust 50 permits the exhaust 36 to communicate via the exhaust line 40 with the flow line aperture 52. Additionally, the intake seal 54 is positioned between the sub-housing connector 53 and the intake line 38, thus allowing the intake 34 to communicate with the valve inlet 48 via the intake line 38. Therefore, air external to the flow line is drawn into the intake sub-housing 46 of the blow-back valve 41 and into the pump module 32 via the intake 34. This air, in turn, is circulated through the pump module 32 and forced out of the exhaust 36 of the pump module 32, through the exhaust line 38, through the exhaust sub-housing 47, through the sub-housing connector 53, and out of the flow-line aperture 52 toward the flow line 26.

The sealing of the valve inlet 48 by the intake seal 54 disposed within the intake sub-housing 46 is illustrated by FIG. 4B. As the cam 60 rotates (in this illustration clockwise), the valve piston 64 is biased away from the exhaust 50 and toward the valve inlet 48. As described above with respect to FIG. 3, once the intake seal is between the intake line 38 and the valve inlet 48, the exhaust seal 55 is between the sub-housing connector 53 and the exhaust line 40. In this configuration, the intake 34 is adapted to communicate with the flow line aperture 52 thus creating a pressure drop between the intake 34 and the breast shield 22 as illustrated in FIGS. 1 and 2 via the flow line 26, the flow line aperture 52, the blow-back valve 41, and the intake line 38. Simultaneously, the exhaust 36 communicates with the valve exhaust 50 disposed in the exhaust sub-housing 47 of the blow-back valve 41. Therefore, the intake 34 of the pump module 32 evacuates the air from the flow line 26 through the intake sub-housing 46 of the blow-back valve 41. The air is drawn through the pump module 32 and forced out of the blow-back valve 41 via the exhaust 36, the exhaust line 40, and the valve exhaust 50.

As the valve cam 60 rotates and forces the valve piston 64 toward the zenith, a load is being applied to the valve-spring 56 disposed between the cam follower 58 and the exhaust sub-housing 47. Upon passing the intake line coupling 42, the intake seal 54 seals the valve inlet 48 from the intake line 38. At this point, the greatest load is applied to the valve-spring 56 during the valve cam 60. Accordingly, when the valve cam 60 continues to rotate to the point at which the valve piston 64 begins to move toward the nadir, the valve spring 56 unloads, thus increasing the velocity of the valve piston 64 and reducing the time required for the valve piston 64 to travel the distance from the zenith to the nadir. This increased velocity and reduced time reduces the time for any overlap in the intake and exhaust phases of the pump/valve assembly 30'.

Figure 4C:
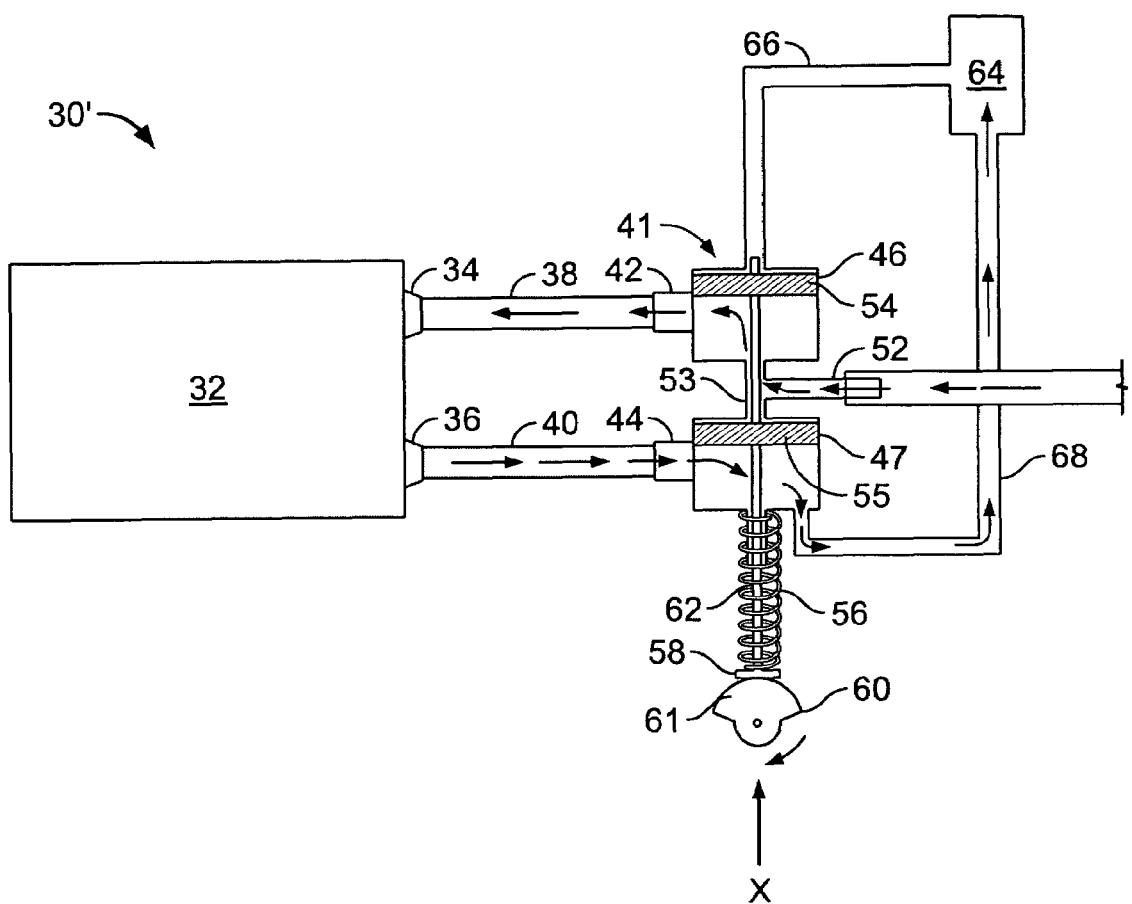
FIG. 4C is a plan view of the single module pump and valve system of FIG. 4B that includes a closed intake and exhaust with a pressure chamber.

FIG. 4C shows an alternative pump/valve system 30' in which the valve inlet 48 and the valve exhaust 50 are connected to a pressure chamber 64 via chamber conduits 66 and 68. When a breast shield 22 (not shown) is placed over the nipple of a breast, the system 30' becomes a closed loop system. Accordingly, instead of the valve exhaust 50 venting to the atmosphere, as in FIGS. 4A and 4B, the exhaust 50 vents to the chamber 66 via chamber conduit 68, and the valve inlet 48 is sealed from the chamber by intake seal 54. Alternatively, when the system cycles to overpressure stage, the exhaust 50 is sealed from the chamber 66 by exhaust seal 55, and air is drawin through the chamber conduit 66 from the chamber 64 through the intake sub-housing 46 to the pump intake 34. Various sizes of chambers 66 may be used in various implementations. With a chamber 66 of appropriate size, wear and tear on the pump module 32 is minimized by maintaining a near-constant load on the pump module 32.

Figure 5A:
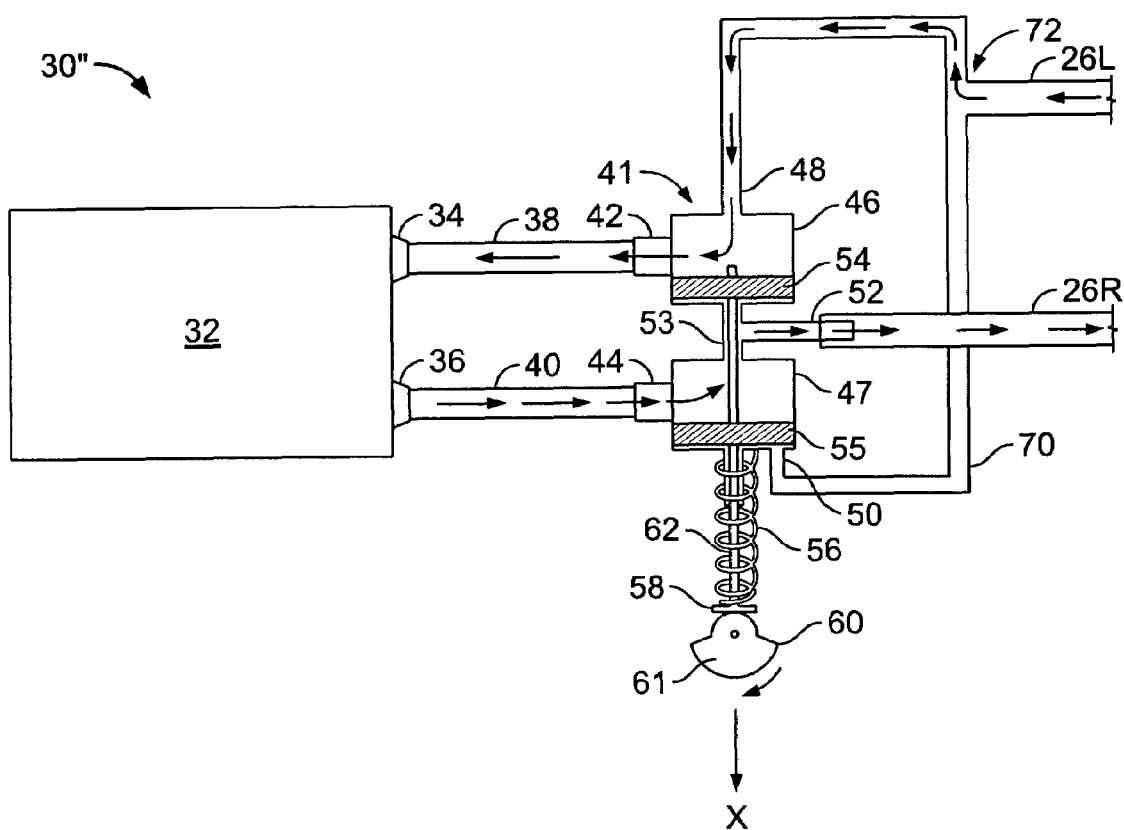
FIG. 5A is a plan view of a single module pump and valve system that provides alternating suction through two flow lines.
Figure 5B:
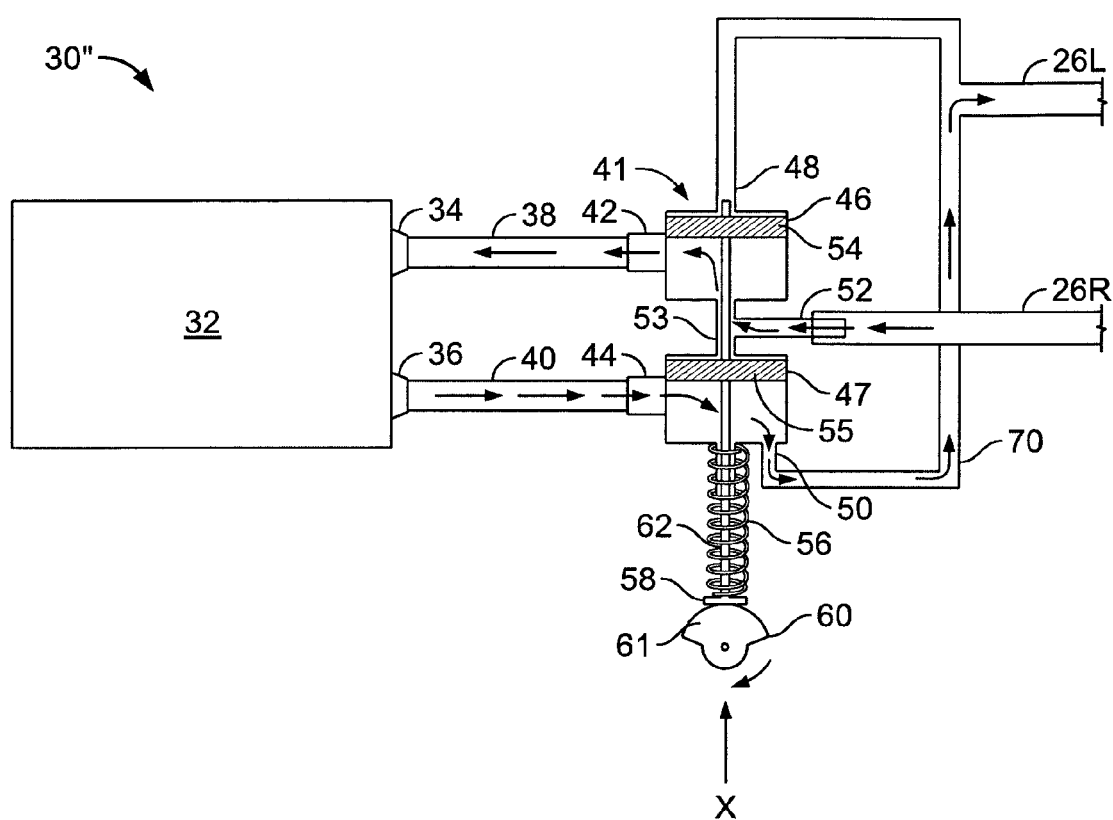
FIG. 5B is a plan view of the single module pump and valve system of FIG. 5A in which the suction/pressure cycle is reversed.

FIGS. 5A and 5B illustrate yet another implementation of a pump/valve system 30" in which two flow lines, 26L and 26R are each connected to a separate breast shield 22 (not shown). The configuration of FIGS. 5A and 5B allows for alternating negative pressure (suction) and positive pressure to be applied to two different breasts. Accordingly, when one breast is being suctioned, the other breast has a positive force of air applied to it.

The pump/valve system 30" includes a flow loop 70 that connects the valve inlet 48 with the valve exhaust 50. Additionally, a t-joint 72 is provided that allows a flow line 26L to alternatively communicate air flow from one of two breasts with the intake 48 and the exhaust 50. In FIG. 5A, the pump/valve assembly, including the piston 62, the intake seal 54, and the exhaust seal 55 are in the "nadir" position, thus allowing the valve inlet 48 to communicate air flow from the flow line 26L to the pump intake 34 via the the intake sub-housing 46 and the intake line 38. Simultaneously, the exhaust seal 55 seals the pump exhaust 36 from the valve exhaust 50 from the flow loop 70 and therefore the flow line 26L. Also, the pump exhaust 36 communicates with the other breast via the flow line aperture 52 and the flow line 26R. Therefore, when the pump/valve system 30" is at the nadir, each of the flow lines 26L and 26R are 180° out of phase. That is, the pump/valve system 30" provides suction through the flow line 26L, while simultaneously providing a positive pressure through the flow line 26R.

FIG. 5B illustrates the pump/valve system of FIG. 5A in which the system 30" is at the zenith, as described above with respect to FIGS. 4A and 4B. Accordingly, the intake seal 54 seals the pump intake 34 from the valve inlet 48 and the flow loop 70 and the flow line 26L. Accordingly, the pump intake 34 communicates with the flow line 26R to provide a suction to the breast shield 22 corresponding to the flow line 26R. Simultaneously, the exhaust seal 55 seals the pump exhaust 36 from the flow line 26R. The exhaust 36 is thus communicable with the flow line 26L to provide a positive pressure to the corresponding breast shield 22 (not shown).

Additional implementations provide the alternating suction/pressure to two breasts though none are presently illustrated. For example, an additional valve housing could be connected to the valve housing 41 of FIGS. 3 and/or 4A and 4B in series. Additionally, the two sets of valve housings could have the valve exhausts and valve inlets closed to make a closed system. Yet another implementation that could provide alternating suction and pressure includes a rotary valve, wherein a cam is provided in a housing that communicates with a pump module and flow lines connected to breast shields to provide simulaneous alternating suction/pressure cycles as illustrated in FIGS. 3 and/or 4A and 4B, or alternating suction/pressure cycles between breasts as illustrated in FIGS. 5A and 5B.

A number of implementations of the invention have been described. Nevertheless, it will be understood that various modifications may be made without departing from the spirit and scope of the invention. For example, various modifications may be made with respect to the valve piston 62, the valve cam 60, the valve seals 54 and 55, as well as other aspects and implementations of the present invention. For example, the valve cam 60 may be of any shape sufficient to impart a phase interval of predetermined specifications for the suction, and/or over pressure phases of the valve/pump assembly 30. Additionally, the exhaust sub-housing and the intake sub-housing may be arranged opposite of their illustrated configuration. Yet another variation includes a different portion of the circumference of the cam 60 encompassed by the lobe 61, thus changing the ratio of suction to non-suction, or in the case of an alternating system, the ratio of the length of time of the suction cycle to one breast versus the other. Accordingly, other implementations are within the scope of the following claims.

What is claimed is:

1. A portable pumping device for drawing milk from a human breast, the device comprising:
    a breast shield adapted to fit over a nipple of a breast;
    a flow line coupled to the breast shield, the flow line adapted to allow air to flow therethrough;
    a pump module coupled to the breast shield via the flow line, a pump intake and a pump exhaust and being operable to create a pressure drop between the nipple and the pump module, wherein the pressure drop creates a suction at the breast shield by lowering the air pressure in the flow line; and
    a blow-back valve disposed between the flow line and the pump intake and the pump exhaust, the blow-back valve constructed to alternatively cycle between connecting the pump intake to the breast shield, in a first position, in which the pump module draws air from the breast shield to generate suction to express breast milk, and to connect the pump exhaust to the breast shield, in a second position, in which the pump module pumps air toward the breast shield through the flow line,
    wherein the blow-back valve has a valve piston disposed in a valve housing, wherein the valve housing includes a flow line aperture that communicates via the flow line with the breast shield, a valve inlet adapted to communicate external to the flow line, and a valve exhaust adapted to communicate external to the flow line, wherein the valve piston is adapted to alternatively seal the valve inlet and the valve exhaust,
    wherein the valve piston comprises an intake seal, an exhaust seal, and a valve plunger wherein the flow line aperture is disposed between the intake seal and the exhaust seal,
    wherein the valve housing includes an intake sub-housing and an exhaust sub-housing, wherein the intake sub-housing is coupled to the pump intake via an intake line and adapted to accommodate the intake seal therein, and wherein the exhaust sub-housing is coupled to the pump exhaust via an exhaust line and adapted to accommodate the exhaust seal therein, and
    wherein when the exhaust seal seals the valve exhaust from the pump exhaust, the pump intake is adapted to communicate with the valve inlet and the pump exhaust is adapted to communicate with the flow line aperture, said communication resulting in an over pressure between the pump and the breast shield.

2. The portable pumping device of claim 1, wherein sealing the valve inlet creates suction at the breast shield and allows air evacuated from the flow line to be dispelled through the valve exhaust.

3. The portable pumping device of claim 1, wherein sealing the valve exhaust draws air through the valve inlet and creates a pressure increase between the flow line aperture and the breast shield.

4. The portable pumping device of claim 1, wherein the intake seal and the exhaust seal are substantially aligned along a valve axis, wherein the movement of the valve plunger along the valve axis within the housing causes the intake seal to seal the valve inlet and causes the exhaust seal to form a seal between the flow line aperture and the pump exhaust.

5. The portable pumping device of claim 1, wherein the intake seal and the exhaust seal are substantially aligned along a valve axis, and wherein the movement of the valve plunger along the valve axis within the housing causes the intake seal to form a seal between the pump intake and the flow line aperture and causes the exhaust seal to form a seal between the pump exhaust and the valve exhaust.

6. The portable pumping device of claim 4, further comprising a cam coupled to the valve plunger, the cam operable to rotate, wherein the rotation of the cam causes the valve plunger to move back and forth substantially along the valve axis.

7. The portable pumping device of claim 6, further comprising a valve spring, wherein the valve spring is disposed between the cam and the valve housing, the valve spring adapted to be loaded when the rotation of the cam forces a spring stop of the valve plunger toward the valve housing, wherein the further rotation of the cam and the loaded valve spring to assist the second seal in sealing the exhaust.

8. The portable pumping device of claim 1, wherein when the intake seal seals the valve inlet from the pump intake, the valve inlet is adapted to communicate with the flow line aperture, and the pump exhaust is adapted to communicate with the valve exhaust, said communications resulting in a suction between the pump and the breast shield.

9. A system for drawing milk from a human breast, the system comprising:
   at least one pump module, a pump intake and a pump exhaust, wherein the pump intake and the pump exhaust are adapted to direct the flow of air through the at least one pump module;
   an intake line coupled to the pump intake;
   an exhaust line coupled to the pump exhaust;
   a valve piston disposed in a valve housing, the valve piston having an intake seal and an exhaust seal, the intake seal and the exhaust seal coupled to a valve plunger, wherein the intake seal is operable to seal a valve inlet in the valve housing, and wherein the exhaust seal is operable to seal a valve exhaust in the valve housing;
   a flow line aperture disposed in the valve housing between the intake seal and the exhaust seal, the flow line aperture adapted to communicate an air flow between the at least one pump module and a breast shield coupled to the valve housing via the flow line, wherein the valve piston cycles to alternatively connect the pump intake to the breast shield, in a first position, in which the pump module draws air from the breast shield to generate suction to express breast milk, and to connect the pump exhaust to the breast shield, in a second position, in which the pump module pumps air toward the breast shield;
   a cam coupled to the valve piston, the cam adapted to rotate, a cam follower disposed at the end of the valve plunger, wherein the cam follower is in contact with the cam, and wherein the rotation of the cam is operable to cause the valve piston to alternatively seal the valve inlet and the valve exhaust by applying a force to the cam follower to move the valve piston back and forth within the valve housing; and
   a sub-housing connector disposed in the valve housing between the intake sub-housing and the exhaust sub-housing, wherein the flow line aperture is disposed through a wall of the sub-housing connector, and
   wherein the intake seal is adapted to form a seal between the intake line and the sub-housing connector, and wherein the exhaust seal is adapted to form a seal between the exhaust line and the valve exhaust, said seals operable to create an over-pressure between the valve and the breast shield.

10. The system of claim 9, further comprising: an intake sub-housing; and an exhaust sub-housing, wherein the intake seal is disposed within the intake sub-housing and wherein the exhaust seal is disposed within the exhaust sub-housing.

11. The system of claim 9, further comprising a valve spring disposed between the cam follower and the valve housing, wherein the cam follower loads the valve spring when the valve plunger is biased toward the valve housing, wherein the valve piston reaches a zenith when the load on the valve spring is greatest, and wherein rotation of the cam causes the valve piston to move away from the zenith.

12. The system of claim 11, wherein the continued rotation of the cam causes the valve spring to unload, the unloading of the valve spring operable to assist the valve piston in moving from the zenith toward a nadir, wherein the nadir is a position of the valve piston distal from the zenith.

13. The system of claim 9, wherein the intake seal is adapted to form a seal between the intake line and the valve inlet, and wherein the exhaust seal is adapted to form a seal between the exhaust line and the sub-housing connector, said seal between the intake line and the valve inlet and said seal between the exhaust line and the sub-housing connector operable to create a suction between the breast shield and the pump module.

14. A system for pumping breast milk, the system comprising:
   at least one pump module, a pump intake and a pump exhaust, wherein the pump intake and the pump exhaust are adapted to direct an airflow through the pump module;
   an intake line coupled to the pump intake;
   an exhaust line coupled to the pump exhaust;
   a valve housing, wherein the valve housing includes an intake sub-housing and an exhaust sub-housing;
   a valve inlet disposed through a wall of the intake sub-housing;
   a valve exhaust disposed through a wall of the exhaust sub-housing;
   a valve piston disposed within the valve housing, wherein the valve piston includes a valve plunger, an intake seal disposed within the intake sub-housing, and an exhaust seal disposed within the exhaust sub-housing, wherein the intake seal is adapted to form a seal between the intake line and the valve inlet, and wherein the exhaust seal is adapted to form a seal between the exhaust line and the valve exhaust;

a flow line aperture disposed through a wall in a sub-housing connector, the sub-housing connector disposed between the intake sub-housing and the exhaust sub-housing, wherein the flow line aperture is adapted to communicate between the pump module and a breast shield; and a cam coupled to the valve piston, the cam operable to rotate, the rotation of the cam operable to move the valve piston back and forth within the valve housing, such that movement of the valve piston back and forth alternatively connects the pump intake to the breast shield, in a first position, in which the pump module draws air from the breast shield to generate suction to express breast milk, and to connect the pump exhaust to the breast shield, in a second position, in which the pump module pumps air toward the breast shield, wherein the movement of the valve piston within the valve housing is operable to alternatively form a seal between the valve inlet and the intake line and form a seal between the valve exhaust and the exhaust line, and wherein forming a seal between the valve exhaust and the exhaust line creates an over-pressure between the pump module and the breast shield.

15. The system of claim 14, wherein forming a seal between the valve inlet and the intake line creates a suction between the at least one pump module and the breast shield.

16. A breast pumping apparatus comprising:
at least one breast shield adapted to receive and seal against a human breast;
a pump module hydraulically coupled to the at least one breast shield by an air flow conduit, the pump module having a pump intake and a pump exhaust; and
a valve disposed along the conduit between the pump module and the at least one breast shield, the valve cyclically operable to: connect the pump intake to the breast shield in a first position, in which the pump module draws air from the at least one breast shield to generate suction to express breast milk, and to connect the pump exhaust to the at least one breast shield in a second position, in which the pump module pumps air toward the at least one breast shield through the air flow conduit,
wherein the valve further comprises:
  a valve housing, wherein the conduit includes at least one flow line connecting the conduit to the at least one breast shield, and wherein each of the at least one flow lines is connected to a portion of the valve housing, wherein the valve housing includes an intake sub-housing and an exhaust sub-housing;
  a cam with a minimum radius operable to rotate, the cam including a lobe having a greater radius than the minimum radius; and
  a valve plunger at least partially disposed within the valve housing, wherein the valve plunger includes a cam follower in contact with the cam, wherein the rotation of the cam causes at least a portion of the valve plunger to move back and forth within the valve housing,
wherein the valve housing comprises:
  a valve exhaust disposed in the exhaust sub-housing;
  a valve inlet disposed in the intake sub-housing; and
  a sub-housing connector adapted to communicate an air flow between the intake sub-housing and the exhaust sub-housing,
wherein the at least one breast shield comprises a first breast shield adapted to connect to one breast of a pair of breasts and a second breast shield to simultaneously connect to a second breast of the pair of breasts, and wherein the at least one flow line includes a first flow line connecting the valve to the first breast shield and a second flow line connecting the valve to the second breast shield,
the breast pumping apparatus further comprising:
  a flow loop connecting the valve inlet with the valve exhaust, wherein the flow loop is adapted to communicate an air flow between the valve inlet and the valve exhaust;
  a T-joint disposed in the flow loop, the T-joint adapted to connect the flow loop to the first breast shield via the first flow line, wherein the second breast shield is connected valve via the second flow line, and wherein when the valve is in the first position, the pump exhaust communicates a positive pressure between the valve and the first breast shield and the pump intake communicates a suction between the valve and the second breast shield, and wherein when the valve is in the second position, the pump exhaust communicates a positive pressure between the valve and the second breast shield and the pump intake communicates a suction between the valve and the first breast shield.

17. The apparatus of claim 16, further comprising:
an intake seal disposed within the intake sub-housing, wherein the intake seal is operable to seal the valve inlet when the valve is in the first position, and wherein the intake seal is operable to seal the pump intake from the at least one flow line when the valve is in the second position; and
an exhaust seal disposed within the exhaust sub-housing, wherein the exhaust seal is operable to seal the pump exhaust from the at least one flow line when the valve is in the first position, and wherein the exhaust seal is operable to seal the valve exhaust from the pump exhaust when the valve is in the second position.

* * * * *